(12) United States Patent
Champagne

(10) Patent No.: US 10,925,336 B2
(45) Date of Patent: *Feb. 23, 2021

(54) GLOVES WITH SENSORY WINDOWS

(71) Applicant: Exsomed Holding Company, LLC, Phoenix, AZ (US)

(72) Inventor: Lloyd P. Champagne, Phoenix, AZ (US)

(73) Assignee: ExsoMed Corporation, Aliso Viejo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/261,275

(22) Filed: Jan. 29, 2019

(65) Prior Publication Data

US 2019/0150538 A1 May 23, 2019

Related U.S. Application Data

(63) Continuation of application No. 15/222,883, filed on Jul. 28, 2016, now Pat. No. 10,188,161, which is a
(Continued)

(51) Int. Cl.
*A41D 13/08* (2006.01)
*A41D 19/00* (2006.01)
(Continued)

(52) U.S. Cl.
CPC ......... *A41D 19/0096* (2013.01); *A41D 13/08* (2013.01); *A41D 13/087* (2013.01);
(Continued)

(58) Field of Classification Search
CPC .... A41D 13/08; A41D 13/082; A41D 13/087; A41D 19/00; A41D 19/015; A63B 71/148; A63B 19/04
See application file for complete search history.

(56) References Cited

U.S. PATENT DOCUMENTS

| 467,974 A | 2/1892 | Healey |
| D467,974 S | 2/1892 | Healey |

(Continued)

FOREIGN PATENT DOCUMENTS

| CH | 643131 | 5/1984 |
| CH | 646858 | 12/1984 |

(Continued)

OTHER PUBLICATIONS

PCT; International Search Report and Written Opinion dated Feb. 25, 2014 in Application No. PCT/US2013/073727.
(Continued)

*Primary Examiner* — Tajash D Patel
(74) *Attorney, Agent, or Firm* — Knobbe, Martens, Olson & Bear, LLP (57) ABSTRACT

A glove that is less prone to slip on the hand, and/or that provides for better tactile sensation, and/or that provides a better outer grip. The glove has an outer surface, an inner surface, and one or more of: ridges, an inner grip material, and one or more sensory windows at places where greater tactile sensation is desired. The inner grip material friction with the skin and/or is tacky to help maintain the glove in position on the hand. The glove may also include an outer material and/or throwing grip material.

25 Claims, 7 Drawing Sheets

Related U.S. Application Data continuation-in-part of application No. 14/542,217, filed on Nov. 14, 2014, now Pat. No. 9,622,523.

(60) Provisional application No. 61/923,953, filed on Jan. 6, 2014.

(51) Int. Cl.
*A41D 19/015* (2006.01)
*A41F 1/06* (2006.01)
*A61B 42/10* (2016.01)

(52) U.S. Cl.
CPC ..... *A41D 19/0006* (2013.01); *A41D 19/0013* (2013.01); *A41D 19/0058* (2013.01); *A41D 19/015* (2013.01); *A41D 19/01558* (2013.01); *A41F 1/06* (2013.01); *A61B 42/10* (2016.02); *A41D 2400/82* (2013.01); *A41D 2600/10* (2013.01); *A41D 2600/20* (2013.01)

(56) References Cited

U.S. PATENT DOCUMENTS

| | | |
|---|---|---|
| 723,348 A | 3/1903 | Wilkins |
| 1,279,855 A | 9/1918 | Garvey |
| D61,479 S | 9/1922 | Rice |
| 1,538,262 A | 5/1925 | Ackerman |
| 1,894,066 A | 1/1933 | Smith |
| 2,036,413 A | 4/1936 | Wendell |
| D100,816 S | 8/1936 | Fuchs |
| 2,075,550 A | 3/1937 | Smith |
| 2,173,734 A | 9/1939 | Sidnell |
| 2,242,318 A * | 5/1941 | Mosier ............... A41D 19/00 2/159 |
| 2,335,871 A | 1/1942 | Milligan |
| D133,927 S | 9/1942 | Balzano |
| 2,434,035 A | 1/1948 | De Laney |
| D164,429 S | 9/1951 | Kress |
| D179,250 S | 11/1956 | Higier |
| 2,838,759 A | 6/1958 | William |
| 3,096,523 A | 7/1963 | Bruchas |
| 3,283,338 A | 11/1966 | Lucian |
| 3,601,816 A | 8/1971 | Pordes |
| 3,649,967 A | 3/1972 | Millman |
| 3,717,146 A | 2/1973 | Halloran |
| 3,728,739 A | 4/1973 | Semp |
| 3,748,792 A | 7/1973 | Lamb |
| 3,789,555 A | 2/1974 | Means |
| 3,867,727 A | 2/1975 | Povlacs |
| 3,872,514 A | 3/1975 | Liebelt |
| 3,872,515 A | 3/1975 | Miner |
| 4,000,524 A | 1/1977 | Rinehart |
| 4,172,293 A | 10/1979 | Vistins |
| 4,175,593 A | 11/1979 | Sack |
| 4,218,778 A | 8/1980 | Stansbury |
| 4,416,026 A * | 11/1983 | Smith ............... A41D 19/0013 2/161.6 |
| 4,441,213 A | 4/1984 | Trumble et al. |
| 4,471,777 A | 9/1984 | McCorkle |
| 4,494,249 A | 1/1985 | Hansson |
| 4,584,722 A | 4/1986 | Levy et al. |
| 4,590,626 A | 5/1986 | Chen |
| 4,594,736 A | 6/1986 | Connelly |
| 4,608,965 A | 9/1986 | Anspach |
| 4,663,783 A | 5/1987 | Obayashi |
| 4,689,832 A | 9/1987 | Mulvaney |
| 4,781,191 A | 11/1988 | Thompson |
| 4,845,780 A | 7/1989 | Reimers |
| 4,901,717 A | 2/1990 | Moore et al. |
| 4,909,789 A | 3/1990 | Taguchi et al. |
| 4,924,530 A | 5/1990 | Tagaya |
| 5,234,299 A | 8/1993 | Giannuzzi |
| 5,312,255 A | 5/1994 | Bauer |
| 5,317,759 A | 6/1994 | Pierce |
| 5,323,490 A | 6/1994 | Yarbrough |
| 5,345,612 A | 9/1994 | Stein |
| 5,345,927 A | 9/1994 | Bonutti |
| D359,381 S | 6/1995 | Henriquez |
| 5,442,816 A | 8/1995 | Seketa |
| 5,443,466 A | 8/1995 | Shah |
| 5,500,956 A | 3/1996 | Schulkin et al. |
| 5,500,957 A | 3/1996 | Stein |
| 5,527,244 A | 6/1996 | Waller et al. |
| D372,578 S | 8/1996 | Chapman |
| 5,636,382 A | 6/1997 | Chopko et al. |
| 5,644,797 A | 7/1997 | Daneshvar |
| 5,667,510 A | 9/1997 | Combs |
| 5,690,633 A | 11/1997 | Taylor et al. |
| 5,692,242 A | 12/1997 | Tekerman et al. |
| D391,683 S | 3/1998 | Heringer |
| 5,728,255 A | 3/1998 | Junius |
| 5,781,931 A | 7/1998 | Lee |
| 5,794,266 A | 8/1998 | Han |
| 5,817,433 A | 10/1998 | Darras |
| 5,853,413 A | 12/1998 | Carter et al. |
| 5,907,870 A | 6/1999 | Monroe et al. |
| 5,946,720 A | 9/1999 | Sauriol |
| 5,965,276 A | 10/1999 | Shlenker et al. |
| 5,983,395 A | 11/1999 | Lei |
| 6,081,928 A | 7/2000 | Bourne |
| 6,187,007 B1 | 2/2001 | Frigg |
| 6,221,006 B1 | 4/2001 | Dubrul et al. |
| 6,231,319 B1 | 5/2001 | Iida et al. |
| 6,231,413 B1 | 5/2001 | Tsukamoto |
| 6,272,687 B1 | 8/2001 | Cunningham |
| 6,306,140 B1 | 10/2001 | Siddiqui |
| 6,415,443 B1 | 7/2002 | Schierenback |
| 6,475,242 B1 | 11/2002 | Bramlet |
| D471,343 S | 3/2003 | Sun |
| 6,575,822 B2 | 6/2003 | Lowe |
| 6,578,205 B1 | 6/2003 | King |
| 6,592,623 B1 | 7/2003 | Bowlin et al. |
| 6,607,530 B1 | 8/2003 | Carl et al. |
| D479,972 S | 9/2003 | Cueto |
| 6,732,378 B2 | 5/2004 | Novak |
| 6,760,923 B1 | 7/2004 | Tate |
| 6,779,199 B1 | 8/2004 | O'Dea |
| 6,808,526 B1 | 10/2004 | Magerl et al. |
| 6,902,735 B1 | 6/2005 | Jacobs et al. |
| D512,549 S | 12/2005 | Benjamin |
| 7,041,106 B1 | 5/2006 | Carver et al. |
| 7,159,246 B2 * | 1/2007 | Tippey ............... A41D 19/0055 2/159 |
| 7,234,170 B2 | 6/2007 | Simic |
| D552,827 S | 10/2007 | Muse |
| 7,293,296 B1 | 11/2007 | Beraznik et al. |
| 7,334,976 B2 | 2/2008 | Dicke |
| RE40,142 E | 3/2008 | Fous |
| D567,476 S | 4/2008 | Harland |
| D598,636 S | 8/2009 | Kleinert |
| D604,027 S | 11/2009 | Kleinert |
| D605,377 S | 12/2009 | House |
| 7,694,352 B2 | 4/2010 | Kogawa et al. |
| 7,802,314 B2 | 9/2010 | Cohen |
| 7,802,316 B2 | 9/2010 | Hofmann |
| D628,767 S | 12/2010 | Bengyak |
| 7,856,670 B1 | 12/2010 | Hazuga et al. |
| 7,874,021 B2 * | 1/2011 | Sunder ............... G06F 3/014 2/16 |
| 7,988,724 B2 | 8/2011 | Salahieh et al. |
| D645,212 S | 9/2011 | Gellis |
| 8,157,803 B1 | 4/2012 | Zirkle, Jr. |
| 8,225,427 B2 | 7/2012 | Bevier |
| 8,336,119 B2 | 12/2012 | Phelps |
| D677,030 S | 2/2013 | Wessels |
| 8,400,256 B2 | 3/2013 | Matthews |
| D680,276 S | 4/2013 | Kleinert |
| D680,695 S | 4/2013 | Lin et al. |
| 8,448,256 B2 | 5/2013 | Borchert et al. |
| 8,453,266 B2 | 6/2013 | Bevier et al. |
| 8,458,815 B1 | 6/2013 | Green |
| 8,458,818 B2 | 6/2013 | Neuser et al. |
| 8,505,115 B2 | 8/2013 | Matsuoka |
| 8,512,615 B1 | 8/2013 | Amdur et al. |

(56) References Cited

U.S. PATENT DOCUMENTS

| | | |
|---|---|---|
| 8,572,765 B2 | 11/2013 | Tao |
| 8,597,337 B2 | 12/2013 | Champagne |
| D707,526 S | 6/2014 | Daniel |
| 8,852,253 B2 | 10/2014 | Mafi |
| 8,856,967 B2 | 10/2014 | Govindasamy et al. |
| 8,864,804 B2 | 10/2014 | Champagne et al. |
| 9,017,404 B2 | 4/2015 | Champagne et al. |
| 9,032,553 B2 | 5/2015 | Bevier et al. |
| D733,972 S | 7/2015 | Szalkowski et al. |
| D733,974 S | 7/2015 | Lawton |
| D735,968 S | 8/2015 | Furlong |
| D739,993 S | 10/2015 | Mathota |
| 9,179,718 B2 | 11/2015 | Anstey |
| D747,070 S | 1/2016 | Kelly |
| D754,929 S | 4/2016 | Champagne |
| 9,323,327 B2 | 4/2016 | Aleksov et al. |
| 9,370,209 B2 | 6/2016 | Hull |
| 9,414,630 B2 | 8/2016 | Schatzberg et al. |
| 9,480,515 B2 | 11/2016 | Champagne |
| 9,539,084 B2 | 1/2017 | Champagne |
| 9,622,523 B2 | 4/2017 | Champagne |
| D787,779 S | 5/2017 | Williams et al. |
| 9,801,422 B2 | 10/2017 | Anstey |
| 9,884,242 B2 | 2/2018 | Kleinert |
| 9,974,611 B2 | 5/2018 | Champagne et al. |
| 10,130,438 B2 | 11/2018 | Champagne et al. |
| 10,143,247 B2 * | 12/2018 | Smith .............. A41D 19/0003 |
| 10,188,161 B2 | 1/2019 | Champagne |
| 10,299,523 B2 | 5/2019 | Champagne et al. |
| D873,500 S | 1/2020 | Champagne et al. |
| 2001/0049529 A1 | 12/2001 | Cachia et al. |
| 2002/0025335 A1 | 2/2002 | Chou |
| 2002/0045897 A1 | 4/2002 | Dixon et al. |
| 2002/0055747 A1 | 5/2002 | Cano et al. |
| 2002/0055749 A1 | 5/2002 | Esnouf et al. |
| 2002/0143337 A1 | 10/2002 | Orbay et al. |
| 2002/0166156 A1 | 11/2002 | Clark et al. |
| 2002/0198527 A1 | 12/2002 | Muckter |
| 2003/0014077 A1 | 1/2003 | Leung |
| 2003/0083661 A1 | 5/2003 | Orbay et al. |
| 2003/0221240 A1 | 12/2003 | Kister et al. |
| 2004/0193217 A1 | 9/2004 | Lubbers |
| 2004/0255362 A1 | 12/2004 | Soerens et al. |
| 2004/0260288 A1 | 12/2004 | Means |
| 2005/0015846 A1 | 1/2005 | Vistins et al. |
| 2005/0075642 A1 | 4/2005 | Felt et al. |
| 2005/0107791 A1 | 5/2005 | Manderson |
| 2006/0005295 A1 | 1/2006 | Mattesky |
| 2006/0129153 A1 | 6/2006 | Klaue et al. |
| 2006/0165506 A1 | 7/2006 | Panasik |
| 2006/0191056 A1 | 8/2006 | Bottcher |
| 2006/0195099 A1 | 8/2006 | Bottlang |
| 2006/0218697 A1 | 10/2006 | Modha et al. |
| 2006/0271061 A1 | 11/2006 | Beyar |
| 2006/0276790 A1 | 12/2006 | Dawson |
| 2007/0027547 A1 | 2/2007 | Rydell et al. |
| 2007/0074331 A1 | 4/2007 | Bitzer |
| 2007/0118947 A1 * | 5/2007 | Lorenzo .............. B42D 9/04 2/21 |
| 2007/0135816 A1 | 6/2007 | Kropf et al. |
| 2007/0209097 A1 | 9/2007 | Iacullo |
| 2007/0282342 A1 | 12/2007 | Niederberger et al. |
| 2008/0000010 A1 | 1/2008 | Erickson et al. |
| 2008/0010718 A1 * | 1/2008 | Richards .......... A41D 19/0013 2/159 |
| 2008/0134411 A1 | 6/2008 | Shapiro |
| 2008/0155726 A1 | 7/2008 | Anclien |
| 2008/0229477 A1 | 9/2008 | McGough |
| 2008/0244808 A1 | 10/2008 | Chaen |
| 2008/0249547 A1 | 10/2008 | Dunn |
| 2008/0249574 A1 | 10/2008 | McCombs et al. |
| 2009/0062868 A1 | 3/2009 | Casutt |
| 2010/0050311 A1 | 3/2010 | Tsai |
| 2010/0077526 A1 | 4/2010 | Smeltzer |
| 2010/0106254 A1 | 4/2010 | Delsignore |
| 2010/0121136 A1 | 5/2010 | Champagne |
| 2010/0130978 A1 | 5/2010 | Orbay et al. |
| 2010/0312286 A1 | 12/2010 | Dell'Oca |
| 2010/0324556 A1 | 12/2010 | Tyber et al. |
| 2011/0130794 A1 | 6/2011 | Vaidya |
| 2011/0258751 A1 | 10/2011 | Matsuoka |
| 2011/0277215 A1 | 11/2011 | Lee et al. |
| 2011/0296582 A1 | 12/2011 | Bevier et al. |
| 2012/0042437 A1 | 2/2012 | Matthews |
| 2012/0047616 A1 | 3/2012 | Wood |
| 2012/0083847 A1 | 4/2012 | Heubner et al. |
| 2012/0221104 A1 | 8/2012 | Altman et al. |
| 2012/0253464 A1 | 10/2012 | Hwang et al. |
| 2012/0253465 A1 | 10/2012 | Missos |
| 2012/0297517 A1 | 11/2012 | Abu-Bakr |
| 2013/0053961 A1 | 2/2013 | Darwin et al. |
| 2013/0060333 A1 | 3/2013 | Gonzalez |
| 2013/0061369 A1 | 3/2013 | Lim |
| 2013/0165979 A1 | 6/2013 | Greenberg et al. |
| 2013/0197592 A1 | 8/2013 | Mafi |
| 2013/0239291 A1 | 9/2013 | Harris |
| 2013/0261662 A1 | 10/2013 | Mayer et al. |
| 2013/0263355 A1 | 10/2013 | Mavraganes |
| 2013/0274879 A1 | 10/2013 | Champagne et al. |
| 2013/0291282 A1 | 11/2013 | Anstey |
| 2014/0020152 A1 | 1/2014 | Yang |
| 2014/0025124 A1 | 1/2014 | Champagne et al. |
| 2014/0067063 A1 | 3/2014 | Bonutti |
| 2014/0150162 A1 | 6/2014 | Guan |
| 2014/0166521 A1 | 6/2014 | Champagne et al. |
| 2014/0208480 A1 | 7/2014 | Champagne et al. |
| 2014/0208481 A1 | 7/2014 | Champagne et al. |
| 2014/0259283 A1 | 9/2014 | Govindasamy |
| 2015/0040288 A1 | 2/2015 | Gaff et al. |
| 2015/0094722 A1 | 4/2015 | Champagne et al. |
| 2015/0094724 A1 | 4/2015 | Champagne et al. |
| 2015/0094777 A1 | 4/2015 | Champagne et al. |
| 2015/0106997 A1 | 4/2015 | Komlos |
| 2015/0173737 A1 | 6/2015 | Champagne et al. |
| 2015/0182325 A1 | 7/2015 | Champagne et al. |
| 2015/0189932 A1 | 7/2015 | Champagne et al. |
| 2016/0081408 A1 | 3/2016 | Hull |
| 2016/0174634 A1 | 6/2016 | Schatzberg |
| 2016/0296263 A1 | 10/2016 | Champagne et al. |
| 2016/0296264 A1 | 10/2016 | Champagne et al. |
| 2016/0338748 A1 | 11/2016 | Champagne et al. |
| 2017/0035553 A1 | 2/2017 | Champagne et al. |
| 2017/0049167 A1 | 2/2017 | Champagne et al. |
| 2017/0143058 A1 | 5/2017 | Champagne et al. |
| 2017/0189090 A1 | 7/2017 | Champagne et al. |
| 2017/0196609 A1 | 7/2017 | Champagne et al. |
| 2017/0231705 A1 | 8/2017 | Madison |
| 2018/0084851 A1 | 3/2018 | Yao et al. |
| 2018/0360143 A1 | 12/2018 | Williams et al. |

FOREIGN PATENT DOCUMENTS

| | | |
|---|---|---|
| DE | 654995 | 1/1938 |
| DE | 2713386 | 11/1978 |
| DE | 102007003645 | 7/2008 |
| EP | 0597223 | 5/1994 |
| EP | 1378205 | 1/2004 |
| EP | 2606843 | 6/2013 |
| EP | 2828409 B1 | 10/2015 |
| EP | 2950739 | 12/2015 |
| FR | 476889 | 9/1915 |
| FR | 1141139 | 8/1957 |
| GB | 2007099 | 5/1979 |
| GB | 2148094 | 5/1985 |
| WO | 1996039055 | 12/1996 |
| WO | WO 1997/33537 A1 | 9/1997 |
| WO | WO 2004/093700 A1 | 4/2004 |
| WO | WO 2005/092226 A1 | 10/2005 |
| WO | WO 2006/105935 A1 | 12/2006 |
| WO | WO 2007/081601 A1 | 7/2007 |
| WO | WO 2007/109140 A1 | 9/2007 |
| WO | WO 2008/063156 A1 | 5/2008 |
| WO | WO 2010/015158 | 12/2010 |
| WO | 2013126727 | 8/2013 |

(56) References Cited

FOREIGN PATENT DOCUMENTS

| WO | WO 2014/011933 A1 | 1/2014 |
| WO | WO 2014/120972 A1 | 8/2014 |
| WO | WO 2015/050895 A1 | 9/2015 |
| WO | WO 2015/050896 A1 | 9/2015 |
| WO | WO 2015/050898 A1 | 9/2015 |
| WO | WO 2015/050902 A1 | 9/2015 |

OTHER PUBLICATIONS

PCT; International Search Report and Written Opinion dated Apr. 17, 2014 in Application No. PCT/US2014/013940.
AU; Examination Report dated Aug. 4, 2017 in AU Application No. 2014212306.
AU; Examination Report dated Jul. 26, 2018 in AU Application No. 2014212306.
EP; Examination Report dated Jun. 26, 2018 in EP Application No. 13811723.9.
EP: Intent to Grant dated Dec. 14, 2018 in EP Application No. EP13811723.9.
USPTO; Non-Final Office Action dated Jun. 17, 2015 in U.S. Appl. No. 14/542,217.
USPTO; Notice of Allowance dated Dec. 10, 2015 in U.S. Appl. No. 29/475,635.
USPTO Non-Final Office Action dated May 18, 2016 in U.S. Appl. No. 14/542,217.
USPTO; Restriction Requirement dated May 20, 2016 in U.S. Appl. No. 14/099,803.
USPTO; Restriction Requirement dated Jun. 17, 2016 in U.S. Appl. No. 14/133,424.
USPTO; Non-Final Office Action dated Oct. 21, 2016 in U.S. Appl. No. 14/133,438.
USPTO; Notice of Allowance dated Oct. 24, 2016 in U.S. Appl. No. 29/557,960.
USPTO; Final Office Action dated Dec. 23, 2015 in U.S. Appl. No. 14/542,217.
USPTO; Non-Final Office Action dated Nov. 2, 2016 in U.S. Appl. No. 14/133424.
USPTO; Notice of Allowance dated Dec. 19, 2016 in U.S. Appl. No. 14/542,217.
USPTO; Non-Final Office Action dated Feb. 7, 2017 in U.S. Appl. No. 14/099,803.
USPTO; Final Office Action dated Mar. 21, 2017 in U.S. Appl. No. 14/133,438.
USPTO; Final Office Action dated Mar. 24, 2017 in U.S. Appl. No. 14/133,424.
USPTO; Final Office Action dated Apr. 12, 2017 in U.S. Appl. No. 14/099,803.
USPTO; Advisory Action dated Apr. 12, 2017 in U.S. Appl. No. 14/133,424.
USPTO; Advisory Action dated Apr. 25, 2017 in U.S. Appl. No. 14/133,438.
USPTO; Non-Final Office Action dated May 5, 2017 in U.S. Appl. No. 14/133,424.
USPTO; Non-Final Office Action dated May 8, 2017 in U.S. Appl. No. 14/133,438.
USPTO; Non-Final Office Action dated May 31, 2017 in U.S. Appl. No. 14/099,803.
USPTO; Final Office Action dated Jun. 26, 2017 in U.S. Appl. No. 14/133,424.
USPTO; Final Office Action dated Jun. 28, 2017 in U.S. Appl. No. 14/133,438.
USPTO; Final Office Action dated Jul. 27, 2017 in U.S. Appl. No. 14/099,803.
USPTO; Non-Final Office Action dated Sep. 26, 2017 in U.S. Appl. No. 14/099,803.
USPTO; Final Office Action dated Nov. 27, 2017 in U.S. Appl. No. 14/099,803.
USPTO; Non-Final Office Action dated Dec. 27, 2017 in U.S. Appl. No. 14/133,424.
USPTO; Non-Final Office Action dated Jan. 4, 2018 in U.S. Appl. No. 14/133,438.
USPTO; Non-Final Office Action dated Jan. 12, 2018 in U.S. Appl. No. 15/427,981.
USPTO; Notice of Allowance dated Jan. 17, 2018 in U.S. Appl. No. 14/099,803.
USPTO; Final Office Action dated Feb. 9, 2018 in U.S. Appl. No. 14/133,438.
USPTO; Notice of Allowance dated Feb. 15, 2018 in U.S. Appl. No. 14/099,803.
USPTO; Final Office Action dated Feb. 28, 2018 in U.S. Appl. No. 14/133,424.
USPTO; Advisory Action dated Apr. 17, 2018 in U.S. Appl. No. 14/133,438.
USPTO; Advisory Action dated Apr. 18, 2018 in U.S. Appl. No. 14/133,424.
USPTO; Non-Final Office Action dated Apr. 20, 2018 in U.S. Appl. No. 15/222,883.
USPTO; Final Office Action dated Jul. 23, 2018 in U.S. Appl. No. 15/427,981.
USPTO; Notice of Allowance dated Sep. 19, 2018 in U.S. Appl. No. 15/222,883.
USPTO; Notice of Allowance dated Jan. 11, 2019 in U.S. Appl. No. 15/427,981.
USPTO; Notice of Allowance dated Feb. 13, 2019 in U.S. Appl. No. 15/427,981.
Healthcare Exam Gloves, posted at tronexcompany.com, posting date not given, [online], [site visited Sep. 26, 2019], available from Internet, URL: https://www.tronexcompany.com/product-solutions/healthcare-exam-gloves-sterile-and-non-sterile/, 2019, in 4 pages.
Protexis Surgical Gloves, posted at cardinalhealth.com, no posting date, [online], [site visited Sep. 26, 2019], available from Internet, URL: https://www.tronexcompany.com/en/product-solutions/healthcare-exam-gloves-sterile-and-non-sterile/, 2019, in 4 pages.

\* cited by examiner

GLOVES WITH SENSORY WINDOWS

CROSS REFERENCE TO RELATED APPLICATIONS

This application is a continuation of, and claims priority to U.S. application Ser. No. 15/222,883, filed on Jul. 28, 2016, which is a continuation-in-part of, and claims priority to, U.S. application Ser. No. 14/542,217, which was filed on Nov. 14, 2014. U.S. Application Publication Nos. 2014/0166521, 2014/0208480, 2014/0208481, and 2015/0189932 are incorporated herein by reference to the extent their respective disclosures are not inconsistent with the disclosure herein.

FIELD OF THE INVENTION

The present invention relates to gloves that include sections that permit more sensatory touch than other sections of the glove, and/or that fit better on the hand, and/or that provide a better outer grip.

BACKGROUND

It is known to provide gloves that have an outer surface configured and/or comprised of a material to provide for a better grip. As an example, in sports, golf gloves are typically made of leather. The outer leather surface provides a better grip on a golf club than bare hands. In football, receivers and runners may use gloves that have a soft and tacky polyurethane outer surface to assist in catching or carrying the football.

In football, as an example, balls are preferably caught with the fingertips. Modern glove designs often have an outer, soft and/or tacky surface (such as urethane), but the inner surface of the glove has not been sufficiently improved. When a ball hits a glove at a high speed, or a defender tries to dislodge the ball from a player's grip, the lack of friction between the skin of the fingers/hand and the inside glove material can cause the glove to slip or slide, especially if sweat is present. This is sometimes called "finger roll," and makes the glove less effective. A glove should preferably remain connected to the hand on the inside, and to the ball (or a tool or other item being gripped) on the outside.

Problems with known gloves are (1) they can slip on the hand because the inner surface does not sufficiently grip the skin, (2) to solve the problem of slipping on the hand, the gloves are sometimes made very tight, which can make them difficult to put on and take off, and limit hand/finger movement when the glove is on, and/or (3) the gloves limit tactile sensation, sometimes because of the thickness or type of material used to construct the glove.

Further, providing a roughened surface on the outside of gloves is known. However, there has been no disclosure of specific materials, and specific locations of the material on the outer portion of a glove, that would optimize the use of such a material.

U.S. Pat. No. 6,902,735, U.S. Application Publication No. 20150106997 A1, U.S. Pat. Nos. 9,032,553, 8,225,427, U.S. Publication Ser. No. 20080229477, U.S. Application Publication No. US20120297517 A1, U.S. Application Publication No. 20130239291 A1, U.S. Pat. No. 8,448,256, U.S. Application Publication Ser. No. 20150040288 A1, U.S. Application Publication Ser. No. 20100077526 A1, and U.S. Application Publication Ser. No 20150106997 A1 show various glove designs.

SUMMARY

A glove according to the invention may include one or more of the following: (a) one or more grip structures on the inside of a glove to help prevent the glove's inner surface from slipping on the hand, (b) inner grip material on the inner surface of the glove that helps prevent the inner surface from slipping on the hand, (c) sensory windows that provide a user with better tactile sensation, and (d) an outer portion, such as a strap, that helps improve the compression of the inner surface of the glove to one or more fingers and/or the thumb. A glove according to aspects of the invention may be used in sports, work, or other applications, and different types of gloves according to the invention may be utilized for different applications and conditions. In other embodiments, a glove according to aspects of the invention may include strategically positioned outer grip features.

Gloves according to the aspects of the invention preferably function with little or no compromised (a) motion of the joints, and/or (b) sensation of the fingertips.

DETAILED DESCRIPTION OF PREFERRED EMBODIMENTS

Figure 1:
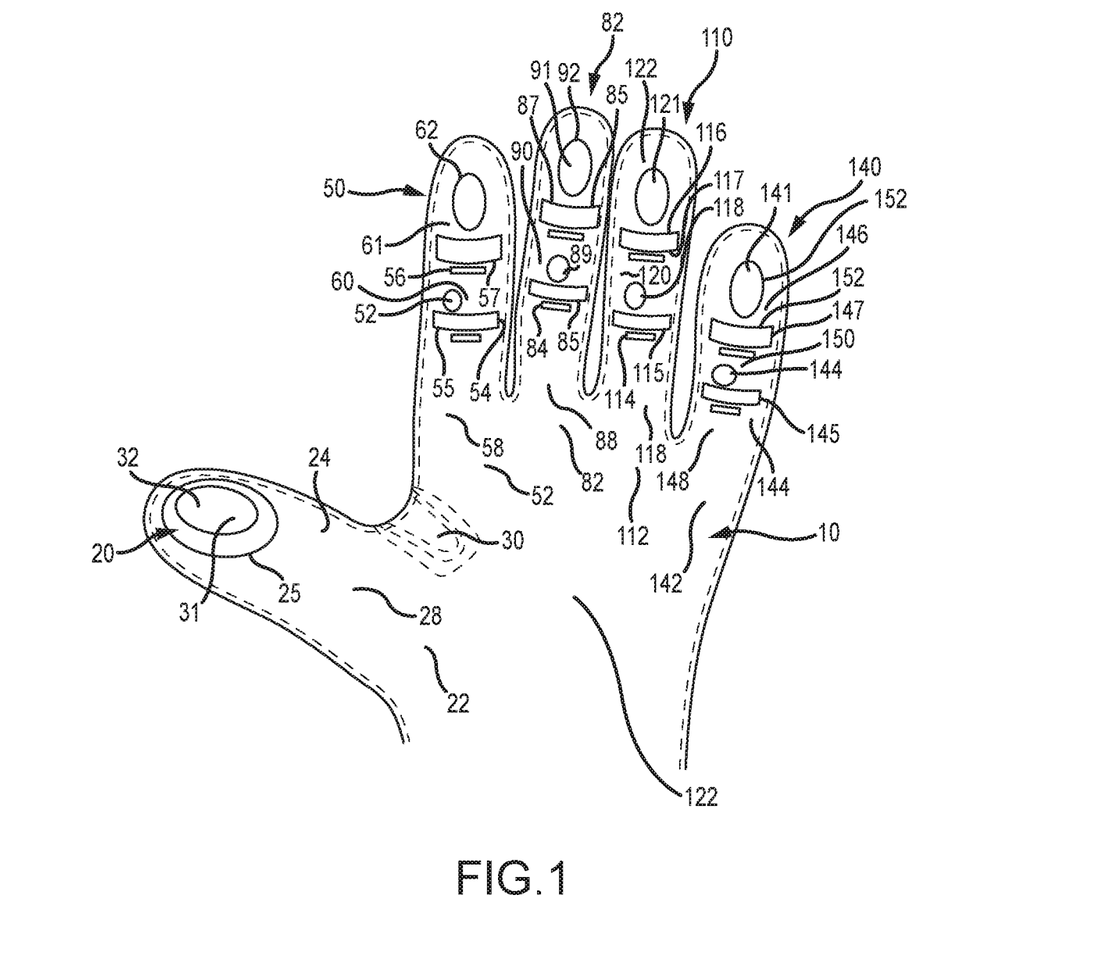
FIG. 1 is a reverse (inside out) front view of a glove in accordance with aspects of the invention.
Figure 2:
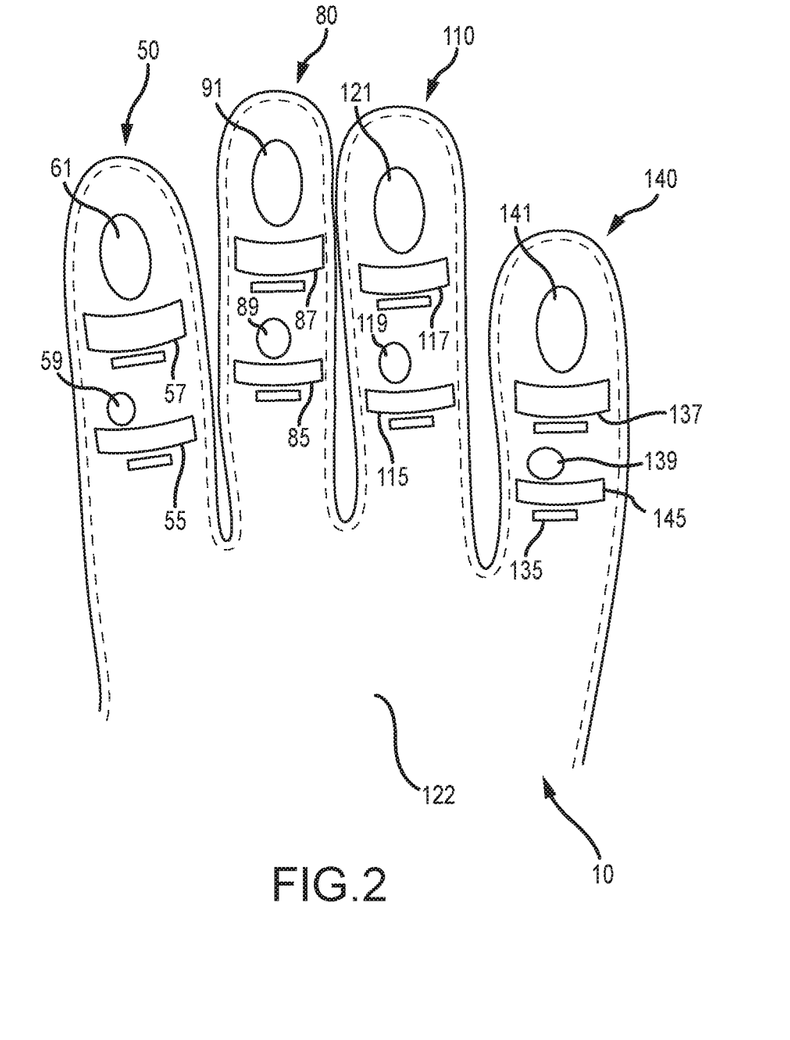
FIG. 2 is another image of the glove of FIG. 1 not showing the thumb portion.

Turning now to the Figures, wherein the purpose is to discuss preferred embodiments of the invention and not to limit same, FIGS. 1-2 show a glove 10 in accordance with aspects of the invention.

Glove 10 has a thumb portion 20, an index finger portion 50, a middle finger portion 80, a ring finger portion 110, a little finger portion 140, a palm side 22, and a dorsum side 24. Each of portions 20, 50, 80, 110, and 140 are sometimes referred to herein singly as a "finger portion" and collectively as "finger portions." The fingers and thumb are sometimes collectively referred to herein as "digits" or singly as a "digit."

Thumb portion 20 has a MCP joint section 22, an IP joint section 24, an area 28 between the MCP joint section 22 and IP joint section 24, and a fingertip area 32. There is also a trapezium area 30 between the thumb portion 20 and index finger portion 50.

Index finger portion 50 has a MCP joint section 52, a DIP joint section 54, a PIP joint section 56, an area 58 between the MCP joint section 52 and DIP joint section 24, an area 60 between the DIP joint section 54 and PIP joint section 56, and a fingertip area 62.

Middle finger portion 80 has a MCP joint section 82, a DIP joint section 84, a PIP joint section 86, an area 88 between the MCP joint section 52 and DIP joint section 24, an area 90 between the DIP joint section 84 and PIP joint section 86, and a fingertip area 92.

Ring finger portion 110 has a MCP joint section 112, a DIP joint section 114, a PIP joint section 116, an area 118 between the MCP joint section 112 and DIP joint section 24, an area 120 between the DIP joint section 114 and PIP joint section 116, and a fingertip area 122.

Little finger portion 140 has a MCP joint section 142, a DIP joint section 114, a PIP joint section 116, an area 118 between the MCP joint section 52 and DIP joint section 24, an area 150 between the DIP joint section 114 and PIP joint section 116, and a fingertip area 152.

The embodiment shown in FIGS. 1-2 includes (a) one or more outwardly-extending ridges (or simply "ridges") on the inner surface of the thumb portion 20 and each finger portion 50, 80, 110, and 140, (b) one or more sensory windows at one or more locations on the inner surface of the glove at the thumb portion 20 and each finger portion 50, 80, 110, and 140, and (3) an inner grip material to provide more friction, or grip, against the skin of the hand and/or fingers. A glove according to the invention, however, need only have one of features (a)-(c).

Ridges

If ridges are utilized, there may be just one ridge per finger/thumb portion, and not every finger/thumb portion need have a ridge. There need only be a single ridge for a single digit portion, such as one ridge for the index finger portion 50. A ridge according to a preferred embodiment is comprised of any suitable material, such as felt, leather, or soft plastic. A ridge according to the invention preferably extends outward from the inner surface by about 0.3 mm to 4 mm, and is compressed to about 0.1 mm to 3.0 mm during normal use. It has any suitable width, such as 0.5 mm to 5 mm. A ridge may also narrow from its base at the inner surface of the glove to its top, to form an essentially triangular blade shape. A ridge may be straight and cross-axial as compared to the longitudinal axis of the digit with which it is associated, and may be circular to extend along the entire circumference of the digit with which it is associated, or it may be semi-circular, or of any suitable length. The purpose of the ridges(s) is to prevent or reduce slippage of the inner surface of the glove against the skin, and any suitable structure using any suitable material, wherein the structure extends outwardly from the inner surface of the glove may be used for this purpose.

As shown in the embodiment of FIGS. 1-2, for the thumb portion 20, there is one ridge 25 above the IP joint portion 24. For the index finger portion 50, there is one ridge 55 above PIP joint portion 54, and one ridge 57 above DIP joint portion 56. For the middle finger portion 80, there is one ridge 85 above PIP joint portion 84, and one ridge 87 above DIP joint portion 86. For the ring finger portion 110, there is one ridge 115 above PIP joint portion 114, and one ridge 117 above DIP joint portion 116. For the little finger portion 140, there is one ridge 145 above PIP joint portion 144, and one ridge 147 above DIP joint portion 146.

A variant to the embodiments discussed above is to add more ridges, which may be semicircular, complete circular, or of any suitable length up and down the inside of one or more digits of the glove and even (or alternatively) on the hand.

Sensory Windows

Sensory windows are preferably used when an inner grip material (discussed below) is included as part of, or added to, the inner surface of a glove. But, a glove according to aspects of the invention need not have an inner grip material to include one or more sensory windows. The sensory windows are areas that do not include the inner grip material, or that include a different inner material than the inner grip, or if an inner grip material is not present at the location that includes the sensory window, includes inner material of a reduced thickness, in order to improve the tactile sensation through the glove. If sensory windows are utilized, there may be just one sensory window per finger/thumb portion, and not every digit portion of the glove need have a sensory window. There need only be a single sensory window for a single digit, such as one for the fingertip area 62 of the index finger portion 50, or one or more sensory windows for each of multiple digits. There may also be a sensory window at one or more areas on the palm.

For the embodiment shown in FIGS. 1-2, for the thumb portion 20, there is one sensory window 31 at thumb tip 32. For the index finger portion 50, there is one sensory window 59 between PIP joint portion 54 and DIP joint portion 56, and one sensory window 61 at fingertip 62. For the middle finger portion 80, there is one sensory window 89 between PIP joint portion 84 and DIP joint portion 86, and one sensory window 91 at fingertip 92. For the ring finger portion 110, there is one sensory window 119 between PIP joint portion 114 and DIP joint portion 116, and one sensory window 121 at fingertip 122. For the little finger portion 140, there is one sensory window 149 between PIP joint portion 144 and DIP joint portion 146, and one sensory window 151 at fingertip 152.

If inner grip material is present in the vicinity of the inner surface that includes a sensory window, no inner grip material is preferably present at the sensory window. If no inner grip material is present, a sensory window may have no inner material, or 50% or less the thickness of inner material, which is discussed below. Alternatively, if a glove utilizes ridges and no inner grip material, there need not be sensory windows, or the sensory windows preferably have no ridges thereon. Or, if a glove, such as a glove of uniform material composition, utilizes no ridges or inner grip material, it may still have sensory windows created by reducing the thickness of the glove material at certain areas, or creating openings in the glove material.

Each sensory window may be of any suitable dimension, shape and material, for the size of the glove, the location of the sensory window, and the purpose for which the glove is being used. For example, the sensory window may be round, oval, oblong, rectangular, or square, or any suitable shape. Further, the relative size and shape of the sensory windows may vary for different digits, and the sensory windows may have a different thickness or material for different uses, digits, or weather conditions.

As shown in the embodiments of FIGS. 1-2, each sensory window at fingertip areas 32, 62, 92, 122, and 162 are oval in shape and cover about 50-75% of each fingertip area. Alternatively, each sensory window at the fingertip areas could cover at least 30% of the fingertip area, or at least 50% of the fingertip area, or at least 75% of the fingertip area, or between 30%-75% of the fingertip area.

Each sensory window 59, 89, 119, 149 between the respective PIP and DIP joints of each digit 50, 80, 110, and 140, is shown as being substantially circular, and covering between about 30%-50% of the area on the palm side of the hand of each digit portion 50, 80, 110 and 140 between the respective PIP and DIP joints. The size of the sensory window at any of these locations may be at least 30% of the area, at least 50% of the area, at least 75% of the area, or between 30%-75% of the area of the palm side of the respective digits.

Inner Grip Material

The purpose of an inner grip material 400 is to help prevent the finger from slipping inside of the glove. Adding inner grip material on the inside surface of the glove interferes with sensation, which is alleviated by optionally including sensory windows, which are discussed above. The inner grip material 400 may be used for some, or all, of the inner surface of the glove. If the inner grip material forms only part of the inner surface, the remainder of the inner surface is called inner material. The inner grip material may be applied on top of the inner material (such as adhesively), or may be formed as a separate part of the inner surface and be adjacent inner material that also forms the inner surface.

The inner grip material 400 of a glove according to the invention includes at least one of three components. First, the inner grip material may have a texture or tackiness (such as fine sandpaper or foamed plastic, such as a polyurethane, or tacky plastic, such as a polyurethane) that grips the skin. Second, the inner grip material may have a thickness that causes one or more finger portions 20, 50, 80, 110, and 140 to fit tighter at the fingertip area, which prevents slippage without effecting joint flexibility. Third, especially with a stiff inner grip material, such as certain sandpaper materials, the inside edge of the inner grip material can form a cup around a fingertip sensory window or other sensory window. As the finger flexes and starts to grab, the edge of the inner grip material digs into the skin and "catches" to prevent it, and hence the glove to which it is a part, from shifting position on the skin.

The inner grip material may be any suitable material that functions in one or more of the manners described above. In one preferred embodiment, the inner grip material grips the skin to some extent and is suitable for touching the skin for the period during which the glove would be worn. Examples are felt, polyurethane, and sandpaper. Sandpaper with fine grit, such as 400 grit or higher (which is unlikely to abrade the skin) may be used. The sandpaper is a "wet or dry" sandpaper that functions when wet. If inner material is also used to form the inner surface of the glove, the inner material grips the skin less than the inner grip material, either because the inner material has a smoother texture, is less tacky, or extends less from the inside surface (i.e., has a lower height as measured on the inside surface) than the inner grip material. For example, a glove may include inner material that is one or more of natural-fiber or sunthetic cloth, felt, or smooth plastic, and an inner grip material that is one or more of a sandpaper material, tacky plastic (such as a polyurethane), a foamed, or sponge-like material (such as a rubber or a polyurethane), a textured plastic, or a coarse cloth. In that case, the inner material may have height on the inner surface that is the same as, greater than (such as a 0.5 mm to 2.0 mm greater than), or less than (such as 0.5 mm to 2.0 mm less than) the inner grip material. Alternatively, the inner material may (if suitable) be of the same material as the inner grip material, but extend less (such as 0.5 mm to 2.0 mm less) from the inner surface than the inner grip material.

As previously stated, preferably no inner grip material is provided at the sensory window areas because it would interfere with the user's tactile sensation. Inner grip material has been shown to function well when positioned between the DIP crease and the fingertips, although the inner grip material may be used at any suitable location. If the inner grip material is stiff it is best not to be in the DIP crease or other joint creases, because that could interfere with finger movement. If the inner grip material is soft, then it could be placed in at least part of the DIP crease or other joint areas.

Figure 3:
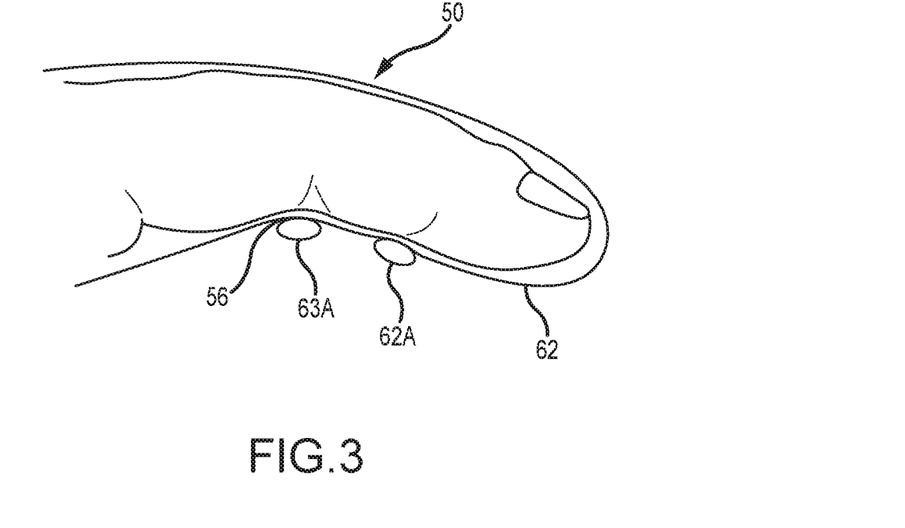
FIG. 3 shows a lateral finger portion of a glove according to the invention.

Referring to FIGS. 1-3, in a manner similar to the grip material distal to the DIP, grip material distal to the PIP helps secure the finger to the glove.

The thicker material works well as there is a natural void of tissue in the creases. Gloves taper to a point at a straight fashion. Fingers, however, taper to the tip in an irregular fashion. There are areas in the cross section of a finger that are relatively large, and which grip and areas with smaller cross sections that tend to be loose in the finger portions of a glove. The volar creases are among these smaller areas, and inner grip material 400 added at the volar creases (as shown in FIG. 3) helps fill the finger portions of the glove to provide a better fit.

Straps

Figure 4:
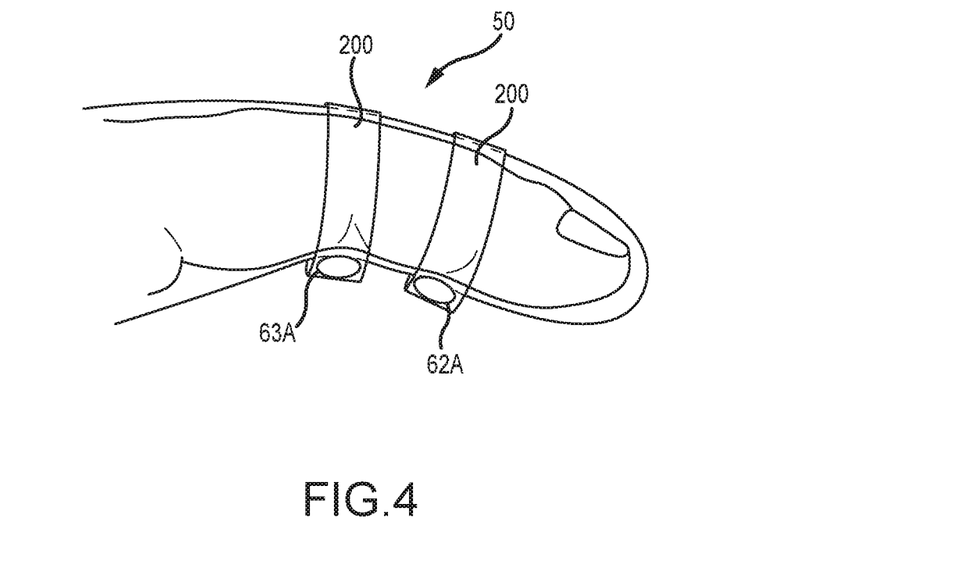
FIG. 4 shows an alternate lateral finger portion of a glove according to the invention.
Figure 5:
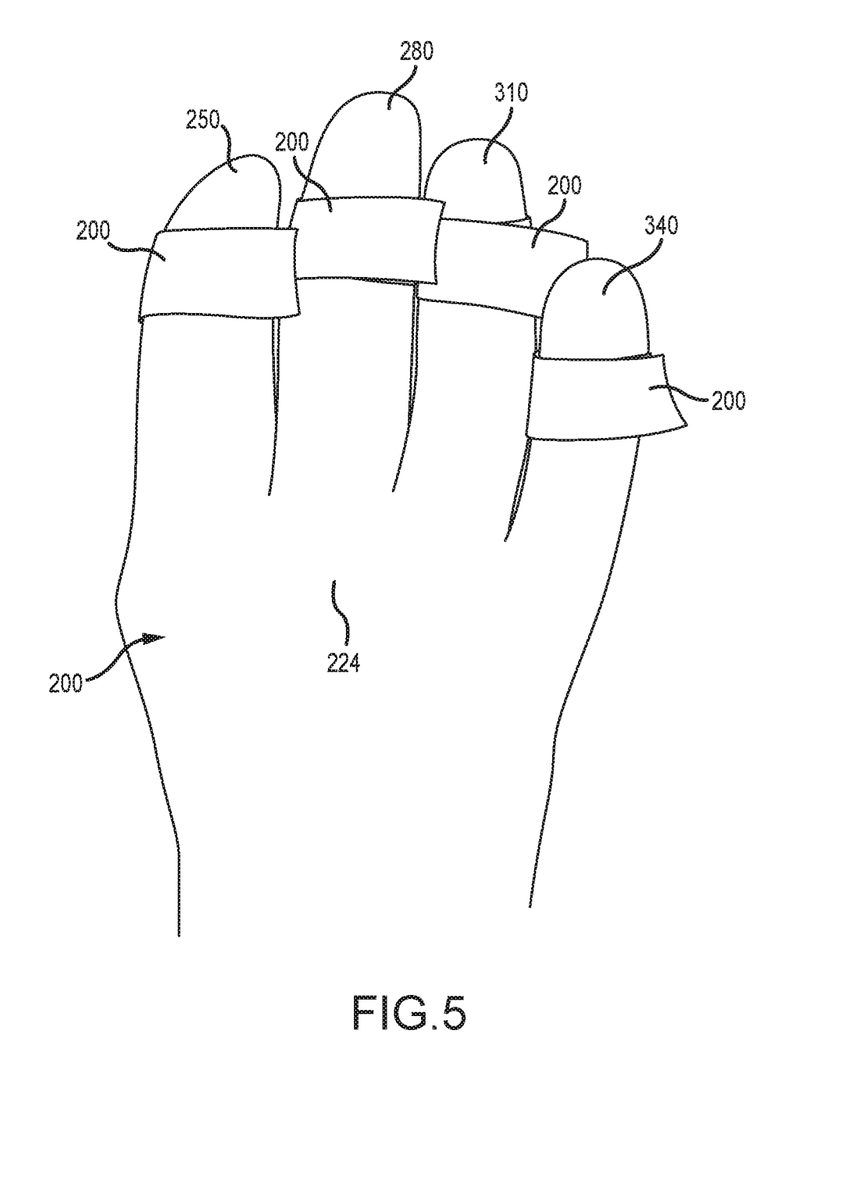
FIG. 5 shows the outside of a glove according to the invention.

FIGS. 4 and 5 show straps 200 on a glove according to aspects of the invention. If used, the straps 200 provide two benefits. The straps wrap around the outside of one or more finger portions 20, 50, 80, 110, and 140 and fasten with Velcro, or in any suitable manner using any suitable material. The use of elastic material as part of the glove to compress a finger portion of the glove to a finger is also within the definition of "strap" herein. The purpose of the one or more straps 200 is to secure the inner surface of glove 10 to each finger portion at which a strap 200 is positioned. Because each of the fingers has a different girth, the straps allow each finger portion (20, 50, 80,110, and/or 140) that includes a strap 200 to be tightened securely to the finger inside of the glove, which presses the inner surface of the glove against the skin of the finger. A strap 200 also tightens any inner grip material to the finger skin, i.e., it presses the sandpaper or other inner grip material against the skin. The location of each strap 200 is selected so it is preferably at the same location as at least some of the inner grip material (if inner grip material is used). A strap 200 is preferably not over a joint, as that would interfere with joint motion. In one preferred embodiment, a strap 200 should be immediately distal to a joint, such as the DIP joint portion of one or more fingers portions 50, 80, 110, and 140, thus tightening the finger portion around the finger tips. At that location, the strap would also tighten the glove around the sensory window (if used) of the glove at the fingertip.

Straps may also, or instead, be used near one or more PIP joint portions 54, 84, 114, and 144, or the IP joint portion 24.

Outer Grip Material

Figure 6:
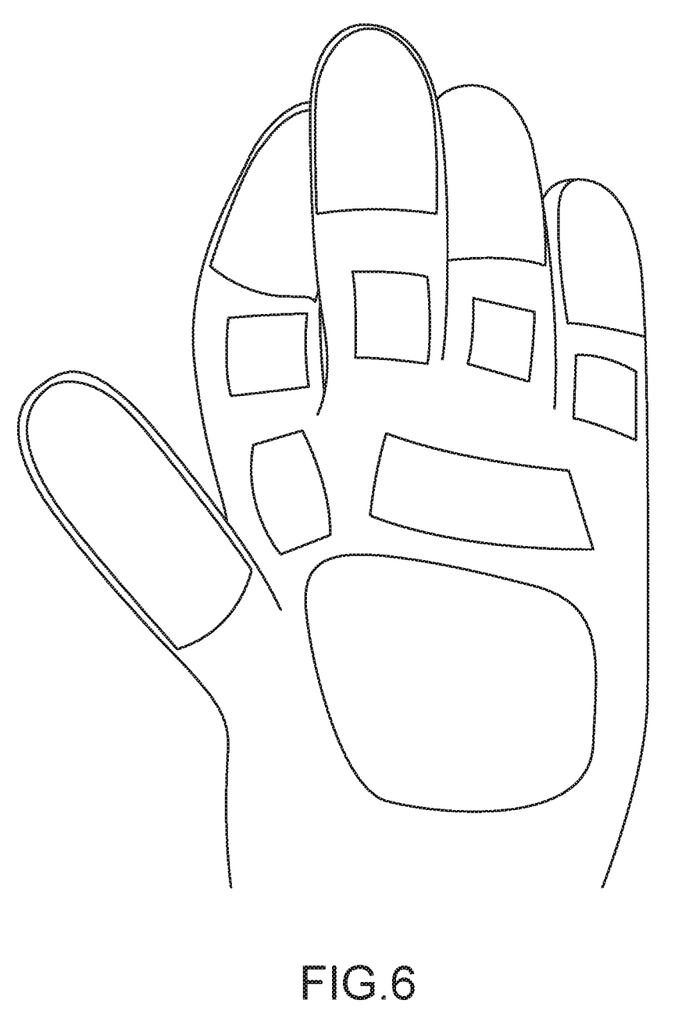
FIG. 6 is an outside view of a glove with roughened surface portions.
Figure 7:
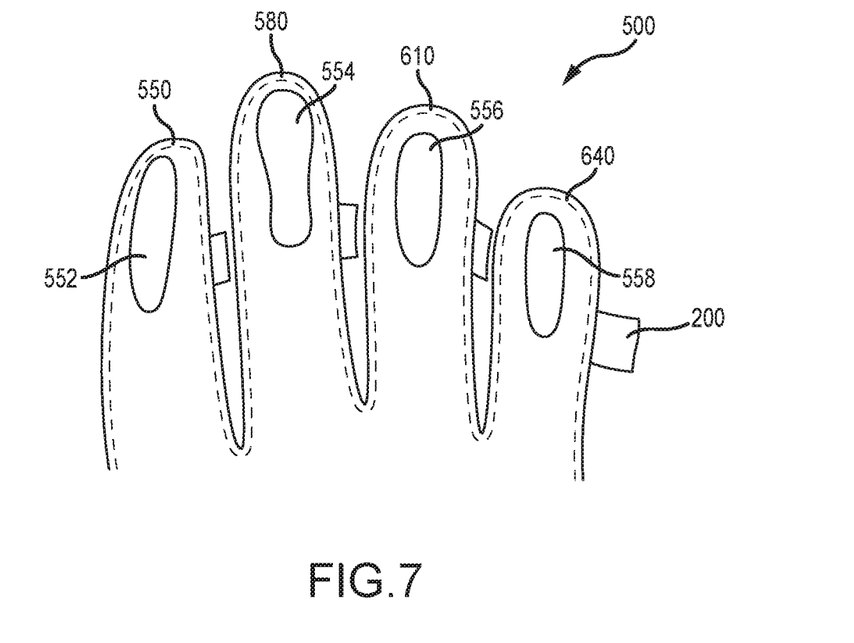
FIG. 7 is an alternate embodiment of a glove with roughened surface portions.

FIGS. 6 and 7 show gripping gloves with exterior features especially suitable for wet, snowy, muddy, or other inclement conditions, but that may be used as part of any glove according to the invention. FIG. 6 is an embodiment that is not preferred because the exterior grip areas are too large. FIG. 7 illustrates a preferred embodiment of a glove 700 according to aspects of the invention. An additional feature is an outer grip material on the outside surface of the glove 300. In one embodiment, this outer grip material is preferably a "wet or dry" sandpaper of grit 200 to 400. This is nontoxic and non-harmful to others, but assists in catching or holding a slippery ball or tool. Any suitable outer grip material, however, may be used, including a tacky material (such as a polyurethane), spongy material (such as a polyurethane), other types of a sandpaper surface or roughened surface. The outer grip material is preferably applied only to the fingertip area of at least one of the finger portions of the glove, preferably from the distal part of the middle phalanx to the fingertip. A strip of about 8 mm running down the middle of the fingertip can be used in one example, although more or less than this amount could be used. No outer grip material is shown in the proximal finger or the palm, although it may be included at either or both locations. The outside grip material is either placed on the outer surface of glove 700, or is formed as part of the outer surface. Glove 700 may include any one or more of the inner glove structures (ridges, sensory windows, and/or inner grip material) described above.

The outer surface of glove 700 preferably includes an outer grip material and an outer material, which is different from the outer grip material. For example, the outer material may be one or more of a nylon or other synthetic fabric, natural-fiber cloth, leather, rubber, or smooth plastic, and the outer grip material may be one or more of a sandpaper material, textured plastic, course synthetic or natural fabric or cloth, tacky material (such as a polyurethane), or a foamed material (such as a polyurethane). The outer grip material provides a better grip against a ball, tool or other structure the glove is to grip or catch than the outer material. Glove 700 may also include one or more outside straps 200 distal to the DIP.

Outer Grip Material for Throwing

Figure 8:
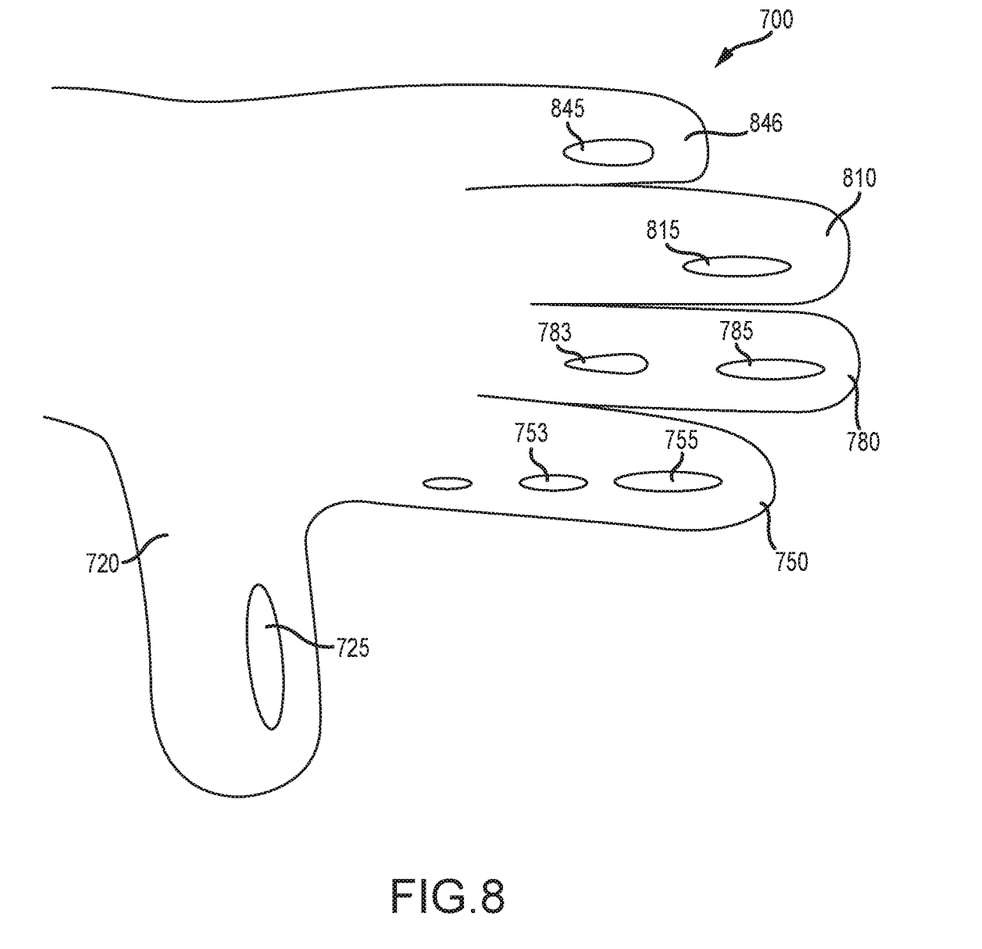
FIG. 8 is a top view of the palm side of a glove designed for throwing.

FIG. 8 shows a glove 800 that may be used for throwing as well as catching, working or other activities. This embodiment includes sandpaper, or another outer grip material 802 (as described above), on the fingertips 820, 850, 880, 910, and 940 and extending along the index and middle finger portions 850 and 880. Glove 800 may include any one or more of the inner glove structures (ridges, sensory windows, and/or inner grip material), described above. As shown in this embodiment, the outer grip material 802 is preferably on the volar and radial side of the finger, but not in the midline. This is the preferred contact area for a football as it rolls off the fingertips, although this contact area for the outer grip material may be adjusted, increased or decreased, as required for different throwers/passers, and for different sports.

Glove 800 can further include outer grip material covering the volar radial finger sleeve of one or more, or a plurality of, or all four finger portions of the glove. The outer grip material on glove 700 is preferably longer on the index finger and middle finger.

SPECIFIC NON-LIMITING EXAMPLES

Some specific, non-limiting examples of gloves according to the invention are as follows:

Example 1

A glove comprising: (a) an outer surface, (b) an inner surface, (c) finger portions, and (d) an outwardly extending ridge on the inner surface of at least one of the finger portions.

Example 2

The glove of example 1 wherein there is an outwardly-extending ridge on the inner surface of a plurality of finger portions.

Example 3

The glove of any of examples 1-2 wherein the ridge is above a DIP joint section of an index finger portion of the glove.

Example 4

The glove of any of examples 1-2 wherein there is a ridge about a DIP joint section of each of the index finger portion, middle finger portion, ring finger portion, and little finger portion of the glove.

Example 5

The glove of any of examples 1-4 that further includes a ridge on the inner surface between a PIP joint portion and DIP joint portion of an index finger portion of the glove.

Example 6

The glove of any of examples 1-4 that further includes a ridge on the inner surface between the PIP joint portion and DIP joint portion of each of the index finger portion, middle finger portion, ring finger portion, and little finger portion of the glove.

Example 7

The glove of any of examples 1-6 wherein the ridge(s) extends outward from the inner surface by 3.0 mm to 6.0 mm.

Example 8

The glove of any of examples 1-7 wherein the ridge(s) is wider at its base than at its top.

Example 9

The glove of any of examples 1-8 wherein the ridge(s) is comprised of one of the group selected from felt, leather, and plastic.

Example 10

The glove of example 1 wherein the ridge is circular and extends around the entire inner surface.

Example 11

The glove of any of examples 1-9 wherein each ridge is circular and extends around the entire inner surface.

Example 12

The glove of any of examples 1-11 wherein the outer surface is comprised of polyurethane or leather.

Example 13

The glove of any of examples 1-12 wherein the inner surface is comprised of leather or felt.

Example 14

The glove of any of examples 1-13 wherein the inner surface further comprises an inner grip material.

Example 15

The glove of example 14 wherein the inner grip material is comprised of one or both of sandpaper and polyurethane.

Example 16

The glove of example 14 or 15 wherein the inner grip material comprises a thick cross-sectional material at one or more fingertip areas.

Example 17

The glove of example 14 wherein the inner grip material is sandpaper of 400 grit or finer.

Example 18

The glove of any of examples 14-17 wherein the inner grip material is proximal to the fingertip area of the index finger portion of the glove.

Example 19

The glove of any of examples 14-17 wherein the inner grip material is proximal to the fingertip area of each of the index finger portion, middle finger portion, ring finger portion, and little finger portion of the glove.

Example 20

The glove of any of examples 14-19 wherein the palm area of the glove includes inner grip material.

Example 21

The glove of example 1 that includes the inner grip material in the palm area.

Example 22

The glove of any of examples 1-21 wherein the ridge is compressed to 0.1 mm to 3.0 mm during use of the glove.

Example 23

The glove of any of examples 1-21 wherein the ridge is compressed to 3.0 mm or less during use of the glove.

Example 24

The glove of any of examples 1-23 that further includes at least one strap to tighten the glove circumferentially around at least one finger portion near the fingertip area.

Example 25

The glove of example 24 wherein the strap is external to the glove.

Example 26

The glove of example 24 or 25 wherein the strap is adjustable.

Example 27

The glove of example 24, 25, or 26 wherein the strap includes one or more of Velcro or elastic.

Example 28

The glove of any of examples 24-27 wherein the width of the strap is 3 cm or less.

Example 29

The glove of any of examples 24-28 wherein the strap is positioned at a location past the PIP joint area of the finger portion.

Example 30

The glove of any of examples 24-29 wherein there is a strap for each of the index finger portion, middle finger portion, ring finger portion, and little finger portion of the glove.

Example 31

The glove of example 30 wherein each strap is positioned beyond the DIP joint portion of each finger portion.

Example 32

The glove of any of examples 1-31 that includes a sensory window on at least one fingertip area of the glove.

Example 33

The glove of any of examples 1-31 that includes a sensory window on a plurality of fingertip areas of the glove.

Example 34

The glove of any of examples 1-31 that includes a sensory window at each fingertip area of the glove.

Example 35

The glove of any of examples 32-34 wherein the sensory window(s) has a shape selected from one or more of the group consisting of circular and oval.

Example 36

The glove of any of examples 32-34 wherein each sensory window has a shape selected from one or more of the group consisting of circular, oval, rectangular, oblong, and square.

Example 37

The glove of any of examples 32-36 wherein there is also a sensory window between the PIP joint area and DIP joint area of the index finger portion.

Example 38

The glove of any of examples 32-36 wherein there is a sensory window between the PIP joint area and DIP joint area on each of a plurality of finger portions.

Example 39

The glove of any of examples 32-38 wherein the sensory window(s) has an area equal to 30% or more of the area of the fingertip.

Example 40

The glove of any of examples 32-39 wherein the sensory window has an area equal to 50% or more of the area of the palm side of the finger between the PIP joint area and the DIP joint area.

Example 41

The glove of any of examples 1-40 wherein there is a relaxed area at each MCP joint.

Example 42

The glove of any of examples 1-41 wherein there is a relaxed area at each PIP joint.

Example 43

The glove of any of examples 1-42 wherein there is a relaxed area at each DIP joint.

Example 44

The glove of any of examples 1-43 wherein there is a relaxed area at each DIP joint.

Example 45

The glove of any of examples 1-44 that further includes outer grip material on the outer surface of the glove to improve grip.

Example 46

The glove of example 45 wherein the outer grip material is selected from one or more of the group consisting of: sandpaper and polyurethane.

Example 47

The glove of example 45 or 46 wherein the outer grip material comprises a textured surface covering the volar radial finger sleeve of a plurality of finger portions.

Example 48

The glove of example 45 or 46 wherein the outer grip material comprises a textured surface covering the volar radial finger sleeve of the index finger portion, middle finger portion, ring finger portion, and little finger portion.

Example 49

The glove of example 48 wherein the external textured surface is longer on the index finger and middle finger than it is on the ring finger and little finger.

Example 50

The glove of any of examples 45-47 wherein the outer grip material is transversely placed extending across each finger volar, or finger dorsal, or both, of the index finger portion, middle finger portion, and ring finger portion of the glove.

Example 51

The glove of any of examples 45-49 wherein the outer grip material is transversely placed extending across at least one finger volar, or finger dorsal, or both.

Example 52

The glove of any of examples 45-49 wherein the outer grip material is transversely placed extending across the finger valor, or finger dorsal, or both, of a plurality of fingers.

Example 53

The glove of any of examples 1-44 that further includes an outer grip material wherein the outer grip material is transversely placed extending across each finger volar, or finger dorsal, or both, of the index finger portion, middle finger portion, and ring finger portion of the glove.

Example 54

The glove of any of examples 1-44 wherein the outer grip material is transversely placed extending across at least one finger volar, or finger dorsal, or both.

Example 55

The glove of any of examples 1-44 wherein the outer grip material is transversely placed extending across the finger valor, or finger dorsal, or both, of a plurality of fingers.

Example 56

The glove of any of examples 1-55 wherein the ridge(s) extends outward from the inner surface by 0.3 mm to 4.0 mm.

Example 57

The glove of any of examples 1-56 wherein the ridge(s) have a width of 0.5 mm to 5.0 mm.

Example 58

The glove of any of examples 1-57 wherein the ridge(s) are narrower at the base then at the top.

Example 59

The glove of example 58 wherein the ridge(s) is in the shape of a triangular blade.

Example 60

A glove having: (a) an inner surface, (b) an outer surface, and (c) finger portions, wherein the glove further includes one or more sensory windows on the inner surface.

Example 62

The glove of example 60 further including any of the structures recited in examples 1-59.

Example 63

A glove having: (a) an inner surface; (b) an outer surface, and finger portions, wherein the glove further includes an inner grip material on at least part of the inner surface.

Example 64

The glove of example 63 further including any of the structures recited in examples 1-59.

Example 65

A glove having: (a) an inner surface, (b) an outer surface, and (c) finger portions, wherein the glove further includes an outer grip material on at least part of the outer surface.

Example 66

The glove of example 65 further including any of the structures recited in examples 1-59.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A glove comprising: an outer surface; an inner surface; finger portions; and a thumb portion; wherein the finger portions comprise an index finger portion including an index fingertip portion having a sensory window wherein there is an outwardly-extending ridge on the inner surface on the finger portions.

2. The glove of claim 1, wherein the finger portions comprise a middle finger portion having a middle fingertip portion, a ring finger portion having a ring fingertip portion, and a little finger portion having a little fingertip portion.

3. The glove of claim 2 that further includes a sensory window at one or more of the middle fingertip portion, the ring fingertip portion, or the little fingertip portion.

4. The glove of claim 1 that further comprises an inner grip material on the inner surface and no inner grip material at the sensor window.

5. The glove of claim 3 that further comprises an inner grip material on the inner surface and no inner grip material at any sensory window.

6. The glove of claim 3 that comprises a sensory window on each of the fingertip portions.

7. The glove of claim 1, wherein the thumb portion comprises a thumb fingertip portion and a sensory window at the thumb fingertip portion.

8. The glove of claim 3, wherein the thumb portion comprises a thumb fingertip portion and a sensor window at the thumb fingertip portion.

9. The glove of claim 1 that further comprises a palm portion and a palm sensory window at the palm portion.

10. The glove of claim 3 that further comprises a palm portion and a palm sensory window at the palm portion.

11. The glove of claim 1, wherein the sensory window has a shape selected from one of the group consisting of circular, oval, oblong, rectangular, and square.

12. The glove of claim 3, wherein each sensory window has a shape selected from one of the group consisting of circular, oval, oblong, rectangular, and square.

13. The glove of claim 1 that further includes a second sensory window between a PIP joint portion and a DIP joint portion of the index finger portion.

14. The glove of claim 3 that further includes a second sensory window between a PIP joint portion and a DIP joint portion of one or more of the middle finger portion, the ring finger portion, or the little finger portion.

15. The glove of claim 1, wherein the sensory window has an area equal to 30% or more of an area of the index fingertip portion.

16. The glove of claim 1, wherein the sensory window has an area equal to 50% or more of an area of the index fingertip portion.

17. The glove of claim 4, wherein the inner grip material is comprised of one or both of sandpaper and polyurethane.

18. The glove of claim 17, wherein the inner grip material is sandpaper of 400 grit or finer.

19. The glove of claim 4, wherein the inner grip material is proximal to the index fingertip portion.

20. The glove of claim 3 that further comprises an inner grip material, wherein the inner grip material is proximal to one or more of the index fingertip portion, middle fingertip portion, ring fingertip portion, and little fingertip portion.

21. The glove of claim 9 that further comprises an inner grip material at the palm portion.

22. The glove of claim 1, wherein there is a relaxed area at each MCP joint portion of each finger portion.

23. The glove of claim 1, wherein there is a relaxed area at each PIP joint position of each finger portion.

24. The glove of claim 1, wherein there is a relaxed area at each DIP joint portion of each finger portion.

25. The glove of claim 1, wherein the index finger portion is comprised of material having a first thickness and the sensory window is comprised of material having a second thickness, the second thickness being less than the first thickness.

* * * * *